(12) United States Patent
Galluppi

(10) Patent No.: US 11,875,545 B2
(45) Date of Patent: Jan. 16, 2024

(54) METHOD AND DEVICE FOR PROCESSING ASYNCHRONOUS SIGNALS GENERATED BY AN EVENT-BASED LIGHT SENSOR

(71) Applicant: GENSIGHT BIOLOGICS, Paris (FR)

(72) Inventor: Francesco Galluppi, Paris (FR)

(73) Assignee: GENSIGHT BIOLOGICS, Paris (FR)

( * ) Notice: Subject to any disclaimer, the term of this patent is extended or adjusted under 35 U.S.C. 154(b) by 856 days.

(21) Appl. No.: 16/961,538

(22) PCT Filed: Jan. 9, 2019

(86) PCT No.: PCT/EP2019/050470
§ 371 (c)(1),
(2) Date: Jul. 10, 2020

(87) PCT Pub. No.: WO2019/137973
PCT Pub. Date: Jul. 18, 2019

(65) Prior Publication Data
US 2021/0383146 A1    Dec. 9, 2021

(30) Foreign Application Priority Data
Jan. 11, 2018  (EP) .................................... 18305020

(51) Int. Cl.
*G06V 10/44*  (2022.01)
*G06V 10/145*  (2022.01)
*A61N 1/36*  (2006.01)

(52) U.S. Cl.
CPC ....... *G06V 10/145* (2022.01); *A61N 1/36128* (2013.01); *G06V 10/44* (2022.01); *A61N 1/36046* (2013.01)

(58) Field of Classification Search
CPC .. G06V 10/145; G06V 10/44; A61N 1/36128; A61N 1/36046; A61N 1/0543; H04N 25/76; H04N 25/70
See application file for complete search history.

(56) References Cited

U.S. PATENT DOCUMENTS 9,987,167 B2   6/2018  Lorach et al.
2014/0085447 A1   3/2014  Lorach et al.
2017/0111619 A1*  4/2017  Benosman ............. G02B 27/18

FOREIGN PATENT DOCUMENTS

EP    3 089 111 A1   11/2016
WO   2007/024391 A2   3/2007
(Continued)

OTHER PUBLICATIONS

Ieng et al., Asynchronous Neuromorphic Event-Driven Image Filtering, Sparse coding of spatio-temporal signals lowers computational cost and raises the efficiency of visual processing, Oct. 2014, Proceedings of the IEEE, pp. 1485-1499 (Year: 2014).*

(Continued)

*Primary Examiner* — Said M Elnoubi
(74) *Attorney, Agent, or Firm* — Faegre Drinker Biddle & Reath LLP

(57) ABSTRACT

A light sensor has a matrix of sensing elements each providing a respective event-based signal sequence including events asynchronously produced as a function of variations of light incident on the sensing element and light level values respectively associated with at least some of the events. The method generates an image comprising pixels corresponding spatially to the sensing elements of the matrix, and determines a set of edge pixels among the pixels of the image. Pixels are selected in response to events included in the event-based signal sequences and for each selected pixel a local contrast measure is evaluated to decide whether or not the selected pixel belongs to the set of edge pixels.

10 Claims, 3 Drawing Sheets

(56) References Cited

FOREIGN PATENT DOCUMENTS

| WO | 2008/022772 A1 | 2/2008 |
|---|---|---|
| WO | 2009/127705 A1 | 10/2009 |
| WO | 2012/153073 A1 | 11/2012 |
| WO | 2013/071231 A1 | 5/2013 |
| WO | 2017/216371 A1 | 12/2017 |

OTHER PUBLICATIONS

Lorach et al., Artificial retina: the multichannel processing of the mammalian retina achieved with a neuromorphic asynchronous light acquisition device, Oct. 2012, Journal of Neural Engineering, vol. 9, No. 6. (Year: 2012).*

Asher et al., "Image Processing for a High-Resolution Optoelectronic Retinal Prosthesis," IEEE Transactions on Biomedical Engineering, Jun. 2007, vol. 54, No. 6, pp. 993-1004.

Asrican et al., "Next-generation transgenic mice for optogenetic analysis of neural circuits," Frontiers in Neural Circuits, Nov. 26, 2013, vol. 7, article 160, pp. 1-10.

Barrett et al., "Optogenetic approaches to retinal prosthesis," Visual Neuroscience, 2014, vol. 31, No. 4-5, pp. 345-354.

Boyden et al., "Millisecond-timescale, genetically targeted optical control of neural activity," Nature Neuroscience, Sep. 2005, vol. 8, No. 9, pp. 1263-1268.

Brandli et al., "ELiseD—An Event-Based Line Segment Detector," 2016 Second International Conference on Event-Based Control, Communication, and Signal Processing (EBCCSP), IEEE, Jun. 13, 2016, pp. 1-7.

Busskamp et al., "Optogenetic therapy for retinitis pigmentosa," Gene Therapy, 2012, vol. 19, No. 2, pp. 169-175.

Curcio et al., "Topography of Ganglion Cells in Human Retina," The Journal of Comparative Neurology, 1990, vol. 300, No. 1, pp. 5-25.

Deisseroth, "Optogenetics," Nature Methods, 2011, vol. 8 (1), pp. 26-29.

Delbruck et al., "Activity-Driven, Event-Based Vision Sensors," Proceedings of 2010 IEEE International Symposium on Circuits and Systems (ISCAS), May 30-Jun. 2, 2010, pp. 2426-2429.

Galluppi et al., "A Stimulation Platform for Optogenetic and Bionic Vision Restoration," 2017 IEEE International Symposium on Circuits and Systems (ISCAS), 2017, 5 pages.

Ieng et al., "Asynchronous Neuromorphic Event-Driven Image Filtering," Proceedings of the IEEE, IEEE, New York, US, vol. 102, No. 10, Oct. 1, 2014, pp. 1485-1499.

Klapoetke et al., "Independent Optical Excitation of Distinct Neural Populations," Nature Methods, 2014, vol. 11, No. 3, pp. 338-346.

Lin et al., "Retinal prostheses in degenerative retinal diseases," Journal of the Chinese Medical Association, 2015, vol. 78, No. 9, pp. 501-505.

Lorach et al., "Artificial retina: the multichannel processing of the mammalian retina achieved with a neuromorphic asynchronous light acquisition device," Journal of Neural Engineering, Institute of Physics Publishing, Bristol, GB, Oct. 17, 2012, vol. 9, No. 6, 13 pages.

Nagel et al., "Channelrhodopsin-2, a directly light-gated cation-selective membrane channel," Proceedings of the National Academy of Sciences, Nov. 25, 2003, vol. 100, No. 24, pp. 13940-13945.

Posch et al., "A QVGA 143 dB Dynamic Range Frame-Free PWM Image Sensor With Lossless Pixel-Level Video Compression and Time-Domain CDS," IEEE Journal of Solid-State Circuits, Jan. 2011, vol. 46, No. 1, pp. 259-275.

Sampsell, "Digital micromirror device and its application to projection displays," Journal of Vacuum Science & Technology B: Microelectronics and Nanometer Structures, 1994, vol. 12, No. 6, pp. 3242-3246.

Scholl et al., "Emerging therapies for inherited retinal degeneration," Science Translational Medicine, 2016, vol. 8 (368), 368rv6, 10 pages.

Stronks et al., "The functional performance of the Argus II retinal prosthesis," Expert Review of Medical Devices, Jan. 2014, vol. 11, No. 1, pp. 23-30.

* cited by examiner

METHOD AND DEVICE FOR PROCESSING ASYNCHRONOUS SIGNALS GENERATED BY AN EVENT-BASED LIGHT SENSOR

CROSS-REFERENCE TO RELATED APPLICATIONS

This application is the U.S. national phase of the International Patent Application No. PCT/EP2019/050470, filed Jan. 9, 2019, which claims the benefit of European Patent Application No. 18305020.2, filed Jan. 11, 2018, the entire content of which is incorporated herein by reference.

FIELD

The present disclosure relates to methods for processing of asynchronous signals generated by event-based light sensors. It further relates to devices, more particularly stimulation devices, implementing said methods and their use in machine vision and management of visual restoration in patients.

BACKGROUND

Contrary to conventional cameras that record successive images at regular sampling instants, biological retinas transmit only very little redundant information on the scene to be visualized, and in an asynchronous manner. Event-based light sensors generating asynchronous signals have been developed from that observation on biological retinas.

An event-based light sensor generating asynchronous signals delivers compressed digital data in the form of events. A presentation of such sensors can be found in "Activity-Driven, Event-Based Vision Sensors", T. Delbrück, et al., Proceedings of 2010 IEEE International Symposium on Circuits and Systems (ISCAS), pp. 2426-2429 or in "A QVGA 143 dB Dynamic Range Frame-Free PWM Image Sensor With Lossless Pixel-Level Video Compression and Time-Domain CDS," Posch et al., 2011, IEEE Journal of Solid-State Circuits, vol. 46, no. 1, pp. 259-275. Event-based vision sensors have the advantage of removing redundancy, reducing latency time and increasing the dynamic range with respect to conventional cameras.

The output of such an event-based light sensor can consist, for each pixel address, in a sequence of asynchronous events that represent changes in the reflectance of the scene at the time they occur. Each pixel of the sensor is independent and detects changes in intensity greater than a threshold since the emission of the last event (for example a contrast of 15% on the logarithm for the intensity). When the change in intensity exceeds the threshold set, an ON or OFF event is generated by the pixel according to whether the intensity increases or decreases. Certain event-based light sensors associate the detected events with measurements of light intensity. Since the sensor is not sampled on a clock like a conventional camera, it can take the sequencing of events into account with very great time precision (for example of about 1 µs). If such a sensor is used to reconstruct a sequence of images, an image frame rate of several kilohertz can be achieved, compared to a few tens of hertz for conventional cameras.

Event-based light sensors have promising perspectives, among others in the field of machine vision and in the field of vision restoration (see, e.g., WO 2012/153073 A1).

The retina is composed of photoreceptors, which are highly specialized neurons that are responsible for photosensitivity of the retina by phototransduction, i.e. the conversion of light into electrical and chemical signals that propagate a cascade of events within the visual system, ultimately generating a representation of world. In the vertebrate retina, phototransduction is initiated by activation of light-sensitive receptor protein (photoreactive protein), rhodopsin.

Photoreceptor loss or degeneration, such as in case of retinitis pigmentosa (RP) or macular degeneration (MD), severely compromises, if not completely inhibits, phototransduction of visual information within the retina. Loss of photoreceptor cells and/or loss of a photoreceptor cell function are the primary causes of diminished visual acuity, diminished light sensitivity, and blindness.

Several therapeutic approaches dedicated to vision restoration in patients suffering from retinal degenerative diseases are currently in development (Scholl et al., 2016, Science Translational Medicine, 8 (368), 368rv6).

For example, visual prosthesis systems comprising a retina implant have been developed which are helpful tools for at least partially re-establishing a modest visual perception and a sense of orientation for blind and visually impaired users by exploiting said fact that, although parts of the retinal tissue have degenerated, most of the retina may remain intact and may still be stimulated directly by light dependent electrical stimuli. Typically, retina implant is implanted into the patient's eye, effecting electrical excitation of the remaining neuronal cells upon light stimulation. When being stimulated, these remaining neuronal cells convey the artificially induced electrical impulses to the visual part of the brain through the optic nerve.

Retinal implants can be broadly divided into two categories: epi- and sub-retinal (Lin et al., 2015, Retinal prostheses in degenerative retinal diseases, J Chin Med Assoc.; 78(9): 501-5). Epi-retinal devices are placed on or near the inner surface of the retina, i.e. the side of the retina which is first exposed to incident light and along which the nerve fibers of the ganglion cells pass on their way to the optic nerve. Epi-retinal implants typically comprise a chip with elements capable of receiving input signal (e.g. infrared light) projected or sent by an extraocular device (typically a camera and a microelectronic circuit) for converting said signal into electrical stimuli via a plurality of stimulation electrodes to stimulate the retinal cells adjacent the chip, in order to restore or improve vision of blind or partially blind patients. In contrast, sub-retinal devices are placed under the retina, between the retina and the underlying retinal pigment epithelium or other deeper tissues; while these sub-retinal devices differentiate from epi-retinal systems, they also rely on the use of elements capable of receiving input signal (e.g. infrared light) projected or sent by an extraocular device.

Alternatively, it has been proposed to restore photosensitivity of the retina of a subject by controlling activity of defined populations of neurons by gene- and neuro-engineering technology termed optogenetics. In contrast to traditional gene therapy that attempts to replace or repair a defective gene or bypass the genetic defect through correction of the protein deficiency or dysfunction, optogenetic approaches can be used to endow normally non-photosensitive cells in the retina with the ability to respond to light, thus restoring useful vision to the patient.

Optogenetics (Deisseroth. Nat Methods 8 (1): 26-9, 2011) refers to the combination of genetics and optics to control well-defined events within specific cells of living tissue. It consists in (i) genetically modifying target cells (e.g. retinal ganglion cells (RGCs) or remaining photoreceptors) in order to render them sensitive to light by the expression of exogenous photoreactive proteins (e.g. opsin), especially in cellular membrane, and (ii) providing illuminating device able to provide light to said photoreactive proteins.

Examples of exogenous photoreactive proteins are provided in WO 2007/024391, WO 2008/022772 or WO 2009/127705 which describe the use of opsin genes derived from plants and microbial organisms (e.g. archaebacteria, bacteria, and fungi) encoding light-activated ion channels and pumps (e.g. channelrhodopsin-2 [ChR2]; halorhodopsin [NpHR]), engineered for expression in mammalian neurons and which can be genetically targeted into specific neural populations using viral vectors. When exposed to light with appropriate wavelength, action potentials can be triggered in opsin-expressing neurons conferring thereby light sensitivity to these cells. Similarly, WO 2013/071231 discloses new channel rhodopsins, Chronos and Chrimson, which have different activation spectra from one another and from the state of the art (e.g., ChR2/VChR1), and allow multiple and distinct wavelengths of light to be used to depolarize different sets of cells in the same tissue, by expressing channels with different activation spectra genetically expressed in different cells, and then illuminating the tissue with different colors of light.

Optogenetics is an extremely powerful tool for selective neuronal activation/inhibition which can, for example, be used to restore neural functions in living animals, including humans (Boyden et al., 2005, *Nature Neuroscience* 8 (9): 1263-68), particularly in the eye (Busskamp et al., 2012, *Gene Therapy* 19 (2): 169-75).

Optogenetic therapy holds the promise to restore visual function in patients affected by retinal degenerative diseases, however, the light-sensitivity of the molecule mediating light responses is much less than the one of endogenous opsins so that no or limited photo-stimulation is expected under natural environmental conditions. Nagel et al (2003, *Proceedings of the National Academy of Sciences* 100 (24): 13940-45) or Klapoetke et al. (2014, *Nature Methods* 11 (3): 338-46) have shown that selected wavelengths of light shall be close to the optimal wavelengths of the photoreactive proteins and Asrican et al. (2013, *Front Neural Circuits*, 2013, 7:160; Busskamp et al. 2012, *Gene Therapy* 19 (2): 169-75) that these photoreactive proteins have a very low sensitivity to light. Therefore in order to obtain minimum level of protein activation by light, the intensity of light received by the target cell or protein shall be above a minimum value (Barrett et al., 2014, *Visual Neuroscience* 31 (4-5): 345-354). As a consequence, an external device providing sufficient irradiance at the right wavelength is mandatory.

Accordingly, both retinal implants and optogenetic therapies rely on two main components. The first component acts directly at retina level, is capable of restoring at least partially light sensitivity, and therefore of transducing received photons (i.e. the input signal) into neural currents: this first component corresponds to the implant in retinal prosthesis systems and to the photoreactive protein genetically introduced and expressed in the retinal cells in optogenetic therapies.

The second component is used to encode visual information, usually acquired through a camera or by arrays of photodiodes, and translate it in the input signal needed by the first component. In retinal implants, the input signal can be current delivered to the retinal layer by a matrix of active electrodes (see, e.g., H. C. Stronks and G. Dagnelie: "The functional performance of the Argus II retinal prosthesis", Expert review of medical devices, Vol. 11, No. 1, pp. 23-30, 2014), or light, e.g. pulse of light, infrared light, capable of activating passive components (see, e.g., A. Asher, et al., "Image processing for a high-resolution optoelectronic retinal prosthesis", IEEE Transactions on Biomedical Engineering, Vol. 54, No. 6, pp. 993-1004, 2007). When optogenetics is used, the input signal is light, delivered at correct intensity and wavelength required to activate the selected photoreactive protein. Regardless of the approach used to restore vision, a stimulation device capable of encoding visual information in real time and transmitting said input signal is needed. More particularly, when said input signal is light it can be generated by a stimulation device comprising a visual frontend, a signal processing unit and a projecting device. Preferably, said visual frontend is an event-based light sensor generating asynchronous signals.

In order to deliver input signal needed by the first component, it is desirable to propose effective signal processing methods applicable to asynchronous signals. Said signal processing methods are implemented by the said signal processing unit.

Stimulation algorithms used to specifically target different populations of cells, so as to emulate their characteristic responses to correctly restore their functionalities have been described for optogenetics (see for example Galluppi et al., 2017, A stimulation platform for optogenetic and bionic vision restoration, IEEE international symposium on circuits and systems (ISCAS). These stimulation algorithms capable of delivering real-time stimulation impose constraints, particularly when the desired resolution is high, as in the case with optogenetics where the transfection can potentially target hundreds of thousands of cells. Thanks to the technological advances in increasing the number of electrodes implantable, retinal implants share the same problem. For example, in the above-mentioned paper "Image processing for a high-resolution optoelectronic retinal prosthesis", Asher, et al., have developed algorithms designed to stimulate bipolar cells in the fovea, and implemented it on a standard computer. They envisage as an output a LCD screen illuminated with pulses of infrared light, which can then be received by the implant. In order to correctly stimulate bipolar cells, they implement algorithms enhancing spatial edges and temporal changes, and arrange the light-emitting component of their stimulating device. These algorithms are expected to operate in real-time, with a frame rate of 25 Hz, on a visual feed provided by a VGA camera. Edge enhancement is performed mimicking the center-surround response of the bipolar cells, modeled as a difference-of-Gaussian filter. Subsequently, data redundancy is reduced by updating output pixels only when input pixels change significantly, as evaluated by comparing subsequent frames. Output pixels are also updated only if their value exceeds a predefined threshold. Importantly, they report a tradeoff in performances, with execution speed increasing for larger thresholds, as fewer input pixels need to be evaluated. This translates however into a greater error in the output image. Finally, they introduced a map of temporal filters to emulate the correct input, in terms of temporal dynamics, for bipolar cells. This is done by evaluating pixel values in a given time interval; all the corresponding frames must therefore be held in memory, so as to be used by the temporal filtering layer.

Nevertheless, this approach of the prior art is not well suited to asynchronous signals generated by event-based light sensors. The native output of event-based light sensor is a series of events: each pixel responds with an event when it detects a local change of light [Posch et al., 2011—supra)]. This stimulation mode, close to natural human retina cell functioning, is therefore a natural candidate for targeting retinal degenerations where RGCs are still functional or optogenetically modified. Nevertheless, one limitation of this system is that movement is required, because if the sensor is not moving or if there is no moving object in the scene, no event is produced, fixed objects disappear, as they do not hold novel information. If the head is fixed, such a stimulus is adequate for parasol cells in retinal periphery, which transiently respond to light change; but this is not adequate to stimulate midget cells, which present a sustained activity as long as there is a difference in their receptive field. This means that, when the head is fixed, rather than having a single event, events need to be produced even when an edge is not moving.

Specific signal processing method is therefore needed which provides sustained stimulation to target cells whenever there is an edge, whether it is moving or not. This stimulation mode is particularly relevant when targeting neurons in the fovea, in which 90% of RGCs are midget cells [Curcio and Allen, 1990, "Topography of ganglion cells in human retina," The Journal of Comparative Neurology, vol. 300, no. 1, pp. 5-25], or when targeting bipolar cells [Asher et al., 2007, "Image processing for a high-resolution optoelectronic retinal prosthesis," IEEE Transactions on Biomedical Engineering, vol. 54, no. 6, pp. 993-1004].

SUMMARY

Disclosed is a method for processing asynchronous signals generated by a light sensor allowing to detect contours in observed scenes, especially when the light sensor is not moving or if there is no moving object in the scene. This signal contour detection can have various applications, for example for pattern recognition. Of particular interest here, though without limitation, is the application to vision restoration.

Accordingly, an object is to provide a signal processing method for detecting contours in scenes observed in the field of view of an event-based light sensors generating asynchronous signals, that may be useful, inter alia, in applications of restoring vision of patients.

A method of processing asynchronous signals generated by an event-based light sensor having a matrix of sensing elements for determining contour representation in scenes is disclosed. The method comprises the steps of:
  receiving, from each sensing element of the matrix, a respective event-based signal sequence including events asynchronously produced as a function of variations of light incident on the sensing element and light level values respectively associated with at least some of the events;
  generating an image comprising pixels corresponding spatially to the sensing elements of the matrix; and
  determining a set of edge pixels among the pixels of the image.

Generating the image comprises updating each pixel of the image based on a light level value associated with a most recent event in the event-based signal sequence received from the sensing element corresponding to said pixel of the image.

Determining the set of edge pixels comprises:
  selecting pixels of the image, wherein the selected pixels comprise pixels selected in response to events included in the respective event-based signal sequences received from the sensing elements;
  evaluating respective local contrast measures with respect to the selected pixels of the image; and
  deciding whether or not the selected pixels belong to the set of edge pixels based on the evaluated local contrast measures.

In an embodiment, the set of edge pixels is repeatedly determined, and the selected pixels comprise each pixel of the image corresponding to a sensing element from which the received event-based signal sequence includes at least one event after the previous determination of the set of edge pixels.

The selected pixels may further include the pixels of the previously determined set of edge pixels. Alternatively, the selected pixels consist only of the pixels selected in response to events included in the respective event-based signal sequences received from the sensing elements.

In an embodiment, the set of edge pixels is determined periodically, with a period in a range of 1 to 100 milliseconds, more preferably in a range of 10 to 100 milliseconds.

A contour representation according to an embodiment may be outputted as a matrix of time-varying bits. In such a representation, each of the time-varying bits of the contour representation corresponds spatially to a respective pixel of the image and has a first value when the respective pixel of the image belongs to the set of edge pixels, and a second value when the respective pixel of the image does not belong to the set of edge pixels.

In the application to vision restoration, the contour representation may be used to control a light modulator such as a digital micromirror device (DMD). According to preferred embodiment, said light modulator is part of the projecting device of a stimulation device as mentioned below. Alternatively, it may be transmitted (e.g. by infrared light) to a retinal implant for stimulation of retina cells.

Another aspect of the present disclosure relates to a signal processing unit that implements the above method. The unit comprises:
  an interface for connecting to a light sensor having a matrix of sensing elements and receiving, from each sensing element of the matrix, a respective event-based signal sequence including events asynchronously produced as a function of variations of light incident on the sensing element and light level values respectively associated with at least some of the events; and
  a processor for generating an image comprising pixels corresponding spatially to the sensing elements of the matrix, and determining a set of edge pixels among the pixels of the image.

The processor is configured to update a respective pixel value of each pixel of the image based on a light level value associated with a most recent event in the event-based signal sequence received from the sensing element corresponding to said pixel of the image. It is also configured to determine the set of edge pixels by:
  selecting pixels of the image, wherein the selected pixels comprise pixels selected in response to events included in the respective event-based signal sequences received from the sensing elements;
  evaluating respective local contrast measures with respect to the selected pixels of the image; and
  deciding whether or not the selected pixels belong to the set of edge pixels based on the evaluated local contrast measures.

According to a special embodiment, the said signal processing unit is configured to alternatively implement either (i) the above disclosed method or (ii) a method of processing the said asynchronous signals generated by an event-based light sensor having a matrix of sensing elements for determining event representation. According to preferred embodiment, said method (ii) is as disclosed in literature, e.g. in US 2014/0085447. More specifically, said method (ii) comprises the steps of:

receiving an input signal representative of a scene to be viewed, the input signal comprising, for each pixel in a matrix of pixels, an event-based asynchronous signal sequence obtained as a function of variations of light relating to the pixel in the scene;

transforming the input signal spatially within the matrix of pixels and temporally along the signal sequences to generate an event representation output signals.

Each of the time-varying bits of the event representation corresponds spatially to a respective pixel of the image and has a first value when an event is included in the respective event-based signal sequence received from the sensing element corresponding to the respective pixel of the image, and a second value when no event is included in the respective event-based signal sequence received from the sensing element corresponding to the respective pixel of the image.

The contour representation keeps the time resolution of the event representation (as each incoming event is integrated in the contour representation), which is in the range of 1 microsecond to 10 milliseconds, more particularly in the range of 0.1 to 10 milliseconds, and the update of each pixel of the contour representation, which is based on local contrast measures, is done with a period in a range of 1 to 100 milliseconds, more particularly in a range of 10 to 100 milliseconds.

In the application to vision restoration, the contour representation and/or the event representation are used to control a light modulator (contour representation mode and event representation mode, respectively), or transmitted to a retinal implant for stimulation of retina cells.

According to preferred embodiment, said signal processing unit in controlled by specific means allowing to select either the use of the contour representation mode or the event representation mode.

Yet another aspect of the present disclosure relates to a computer program product comprising stored instructions to be executed in a processor associated with a light sensor having a matrix of sensing elements, so as to carry out the above method. That is to say, execution of the instructions by the processor controls steps of:

receiving, from each sensing element of the matrix, a respective event-based signal sequence including events asynchronously produced as a function of variations of light incident on the sensing element and light level values respectively associated with at least some of the events;

generating an image comprising pixels corresponding spatially to the sensing elements of the matrix; and determining a set of edge pixels among the pixels of the image.

Generating the image comprises updating each pixel of the image based on a light level value associated with a most recent event in the event-based signal sequence received from the sensing element corresponding to said pixel of the image. Determining the set of edge pixels comprises:

selecting pixels of the image, wherein the selected pixels comprise pixels selected in response to events included in the respective event-based signal sequences received from the sensing elements;

evaluating respective local contrast measures with respect to the selected pixels of the image; and deciding whether or not the selected pixels belong to the set of edge pixels based on the evaluated local contrast measures.

Another aspect of the present disclosure relates to a stimulation device comprising a visual frontend, a signal processing unit and a projecting device.

According to preferred embodiment, said visual frontend consists of an event-based light sensor, more specifically an event-based light sensor having a matrix of sensing elements. According to a special embodiment it is an ATIS (Asynchronous Time-based Images Sensor) neuromorphic silicon retina (Posch et al., 2011, "A QVGA 143 dB Dynamic Range Frame-Free PWM Image Sensor With Lossless Pixel-Level Video Compression and Time-Domain CDS," IEEE Journal of Solid-State Circuits, vol. 46, no. 1, pp. 259-275).

According to preferred embodiment, said processing unit consists of an ARM-based embedded Linux system running an event-based filtering chain. The system communicates with an FPGA board handling the low level management of the ATIS and the DMD through a PCI-e link and is abstracted in a Linux driver. Information received from the event-based light sensor is passed through a filtering pipeline and then sent to control a light modulator, such as a digital micromirror device (DMD), for projection. This filter pipeline handles the noise reduction, the size of the retinal portion to be illuminated and the light pulse dynamics for each pixel, so as to comply with the electro-physiological properties of the reactivated ion channels in the target cell. The filtering pipeline also handles the methods above-described for processing asynchronous signals generated by a light sensor.

According to preferred embodiment, said projecting device comprises a light source associated with a projector controlling said light source (e.g. Texas Instrument Light-Crafter projector) and a light modulator such as a digital micromirror device (DMD) (e.g. DLP3000 Digital Micromirror Device) (Sampsell, 1994, "Digital micromirror device and its application to projection displays," Journal of Vacuum Science & Technology B: Microelectronics and Nanometer Structures, vol. 12, no. 6, p. 3242). The DMD comprises a 680×604 array of mirrors that can switch every 0.7 ms between two discrete angular positions named ON and OFF, with the ON position permitting to reflect the incoming light towards the target. Processed events are encoded by setting the corresponding mirror ON. According to another embodiment, said projecting device is the device disclosed in patent application PCT/EP2017/064827.

Embodiments further relate to the use of a stimulation device in management of visual restoration in patients suffering from retinal degenerative diseases. According to a special embodiment, the stimulation device further comprises means allowing the said patient to select either the use of the stimulation device according to the contour representation mode or to the event representation mode based on the condition of use: if the sensor is not moving or if there is no moving object in the scene (e.g. when reading) the patient can select the contour representation mode, and if the sensor is moving (e.g. when walking in a natural environment) or if there are moving objects in the scene the patient can select the event representation mode.

Other features and advantages of the method disclosed herein will become apparent from the following description of non-limiting embodiments, with reference to the appended drawings.

DETAILED DESCRIPTION

Figure 1:
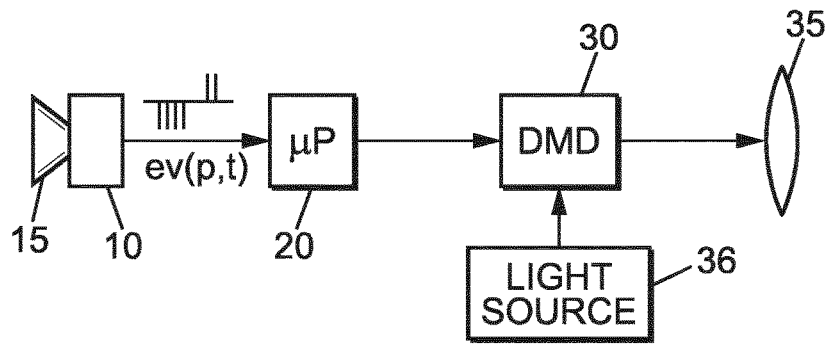
FIG. 1 is a block diagram of a system to which an embodiment of the disclosure may be applied.

The system shown in FIG. 1 comprises an event-based asynchronous vision sensor 10 placed facing a scene and receiving the light flow of the scene through acquisition optics 15 comprising one or more lenses. The sensor 10 is placed in the image plane of the acquisition optics 15. It comprises a group of photosensitive elements organized into a matrix of pixels. Each pixel corresponding to a photosensitive element produces successive events depending on variations of light in the scene.

A processor 20 processes the asynchronous information originating from the sensor 10, i.e. the sequences of events ev(p, t) received asynchronously from the photosensitive elements p, in order to control an output device 30 (e.g. a signal processing unit). The processor 20 operates on digital signals. It can be implemented by programming a suitable processor. A hardware implementation of the processor 20 using specialized logic circuits (ASIC, FPGA, . . . ) is also possible.

In an exemplary application of the method disclosed herein, the system shown in FIG. 1 is used for vision restoration. The output device 30 may be a retinal implant (including epi and subretinal implants) or a projecting device. Alternatively, as illustrated in FIG. 1, the output device 30 forms an image to be projected into the eye of a patient through projection optics 35 comprising one or more lenses.

Preferably, the output device 30 comprises a light modulator, for example a DMD 30 that applies spatial modulation to light from a source 36 which may be an LED-based source. The optics 35 transmits the modulated light to retina cells. In an application of the method, the retina cells receiving the modulated light have been genetically engineered to express photoreactive protein. Thus, reception of the modulated light will cause stimuli through the optical nerve of the patient to restore some form of vision. Alternatively, the modulated light can be transmitted to retinal implant (including epi and subretinal implants).

The light sensor 10 and the output device 30 may be mounted, together with the processor 20 and the optics 15, 35, on goggles to be worn by the patient. Other architectures are possible. The processor 20 may be a separate component, or it may be part of the same component as the sensor 10 and/or the output device 30.

For each sensing element p of the matrix, the sensor 10 generates an event-based asynchronous signal sequence using the variations of light detected by the sensing element in the scene that appears in the field of vision of the sensor.

The asynchronous sensor carries out an acquisition to output information which may be in the form of a succession of instants $t_k$ (k=0, 1, 2, . . . ) at which an activation threshold Q is reached. Each time this intensity increases by a quantity equal to the activation threshold Q starting from what it was in time $t_k$, a new instant $t_{k+1}$ is identified and a spike is emitted at this instant $t_{k+1}$. Symmetrically, each time that the intensity observed by the sensing element decreases by the quantity Q starting from what it was in time $t_k$, a new instant $t_{k+1}$ is identified and a spike is emitted at this instant $t_{k+1}$. The asynchronous signal sequence for the sensing element includes in a succession of spikes positioned over time at instants $t_k$ depending on the light profile for the sensing element. The output of the sensor 10 is then in the form of an address-event representation (AER).

The activation threshold Q can be fixed, or can be adapted as a function of the light intensity. For example, the threshold can be compared to the variations in the logarithm of the light intensity for generating events when exceeded.

An example of an asynchronous sensor that can be used advantageously in the context of an embodiment is the asynchronous time-based image sensor (ATIS) of which a description is given in the article "A QVGA 143 dB Dynamic Range Frame-Free PWM Image Sensor With Lossless Pixel-Level Video Compression and Time-Domain CDS", C. Posch, et al., IEEE Journal of Solid-State Circuits, Vol. 46, No. 1, January 2011, pp. 259-275.

Figure 2:
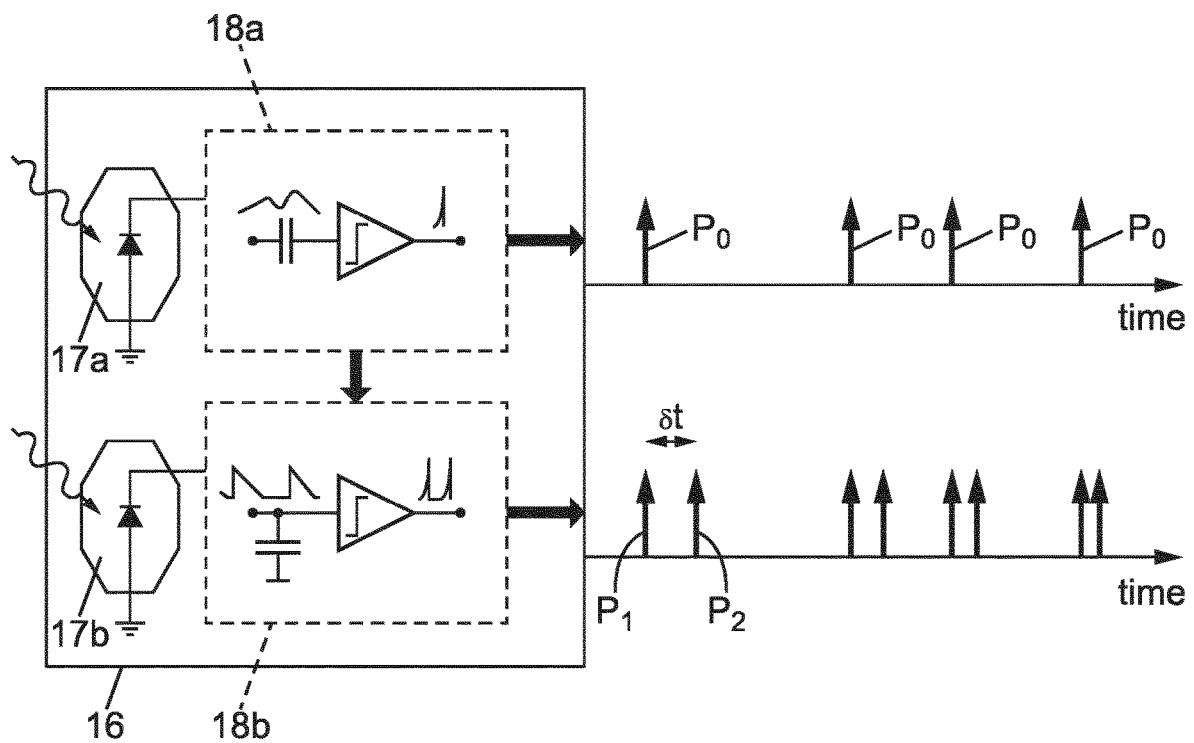
FIG. 2 is a block diagram of an asynchronous light sensor of the ATIS type.

FIG. 2 shows the principle of the ATIS. A sensing element 16 of the matrix constituting the sensor comprises two photosensitive elements 17a, 17b, such as photodiodes, respectively associated with electronic detection circuits 18a, 18b. The sensor 17a and its circuit 18a produce a spike $P_0$ when the light intensity received by the photodiode 17a varies by a predefined quantity Q. The spike $P_0$ that marks this change in intensity triggers the electronic circuit 18b associated with the other photodiode 17b. This circuit 18b then generates a first spike $P_1$ followed by a second spike $P_2$ as soon as a given quantity of light (number of photons) is received by the photodiode 17b. The time shift δt between the spikes $P_1$ and $P_2$ is inversely proportional to the light intensity received by the sensing element 16 just after the appearance of the spike $P_0$.

The asynchronous information originating from the ATIS is a form of AER representation, comprising two spike trains for each sensing element: the first train of spikes $P_0$ indicates the events, namely the instants when the light intensity has changed beyond the detection threshold, while the second train is comprised of spikes $P_1$ and $P_2$ having between them a time shift δt that indicates the corresponding light level values.

The signal sequence coming from a sensing element of address p in the matrix of the ATIS is made of events ev(p, t) comprising two types of information: time information given by the position of the spike $P_0$, giving the instant t of the event, and light level information given by the time shift δt between the spikes $P_1$ and $P_2$ associated with the spike $P_0$.

The light level information from the different sensing elements of the matrix can be combined to form an image of the scene being viewed by the light sensor 10. In general, the image has one pixel p for each sensing element of the matrix, and the pixel value I(p) is given by the light level value (inversely proportional to δt) associated with the most recent coming from the sensing element. If some spatial filtering is applied, the resolution in the image can, however, be different from that of the light sensing elements of the sensor 10.

Figure 3C:
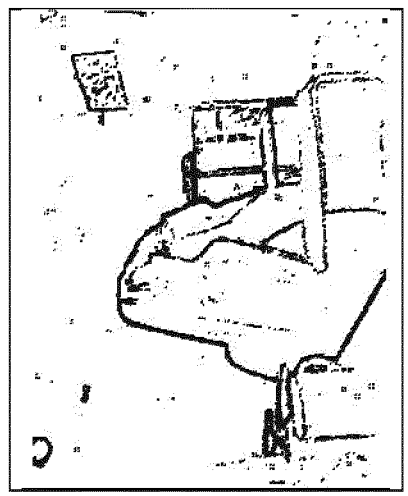
FIGS. 3A, 3B and 3C are images to illustrate an output of the signal processing method in an exemplary embodiment.
Figure 3B:
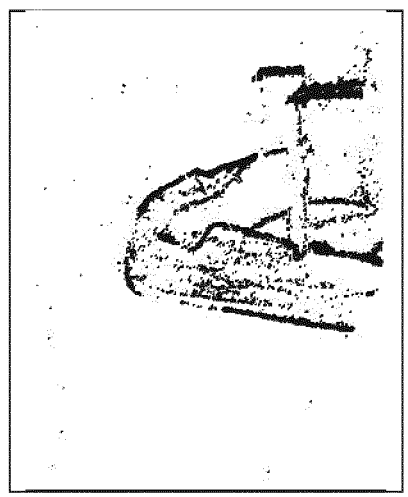
Figure 3A:

FIG. 3A illustrates such a grayscale image (showing a coat on a chair) built from the output signal of an ATIS.

When the scene changes (for example the chair is rotated), the sensor generates spikes $P_0$ which can be viewed as dots in an "event representation" as illustrated in FIG. 3B. The dots can be displayed by activating corresponding micromirrors of the DMD 30 if such a output device comprising light modulator is used. If the ATIS and the DMD do not have the same spatial resolution, some filtering and/or extrapolation can be applied before displaying the dots.

The event representation can be generated as a matrix [V(p)] of time-varying bits V(p), each of which corresponds spatially to a respective pixel p of the image. A time-varying bit V(p) of the event representation, corresponding to a pixel p, has a first value, e.g. '1', when there is an event in the event-based signal sequence received from the sensing element of the sensor 10 that corresponds to pixel p, and a second value, e.g. '0' otherwise.

Such event representation corresponds to the native output of the ATIS silicon retina as a series of events inspired by the response to contrast of retinal ganglion cells. These neurons respond transiently (and with low latency) to light on/offsets or moving edges. The same happens to a sensing element of the ATIS, which responds with an event (spike) when it detects a local change of light. This event-triggered stimulation is therefore a natural candidate for targeting degenerations in the retinal periphery, where parasol ganglion cells are dominant.

When the light sensor 10 does not move, fixed objects in the scene disappear from the content displayed in the event representation, as they do not carry novel information. While this is an adequate stimulation for parasol cells, it is not adapted to the way midget cells respond, as they have a sustained output as long as a difference is present in their receptive field. This means that, rather than having a single event (or emitting a single action potential), stimuli need to be produced even when the edges are not moving.

In order to produce a related excitation, suitable for midget cells, the output device 30 can be further controlled to display contours of objects visible in the scene in a "contour representation". The method disclosed herein is suitable for determining such a contour representation from the output of an asynchronous event-based light sensor.

The contour representation can also be generated as a matrix [E(p)] of time-varying bits E(p), each of which corresponds spatially to a respective pixel p of the image. A time-varying bit E(p) of the contour representation, corresponding to a pixel p of the image, has a first value, e.g. '1', when it is determined that pixel p belongs to a set of edge pixels identified in the scene, and a second value, e.g. '0' otherwise.

FIG. 3C, to be compared with FIGS. 3A and 3B, shows the edge pixels as dots which are displayed in the contour representation. Fixed edges visible in the scene (mug in the foreground, furniture in the background, frame on the wall, etc.) appear in the contour representation and not in the event representation. On the other hand, many dots included in the event representation in areas of low image contrast are not present in the contour representation.

For controlling the output device 30 and more particularly the light modulator comprised in it, the processor 20 may output the event representation, the contour representation, or both, depending on which type(s) of retinal cells need to be stimulated.

Figure 4:
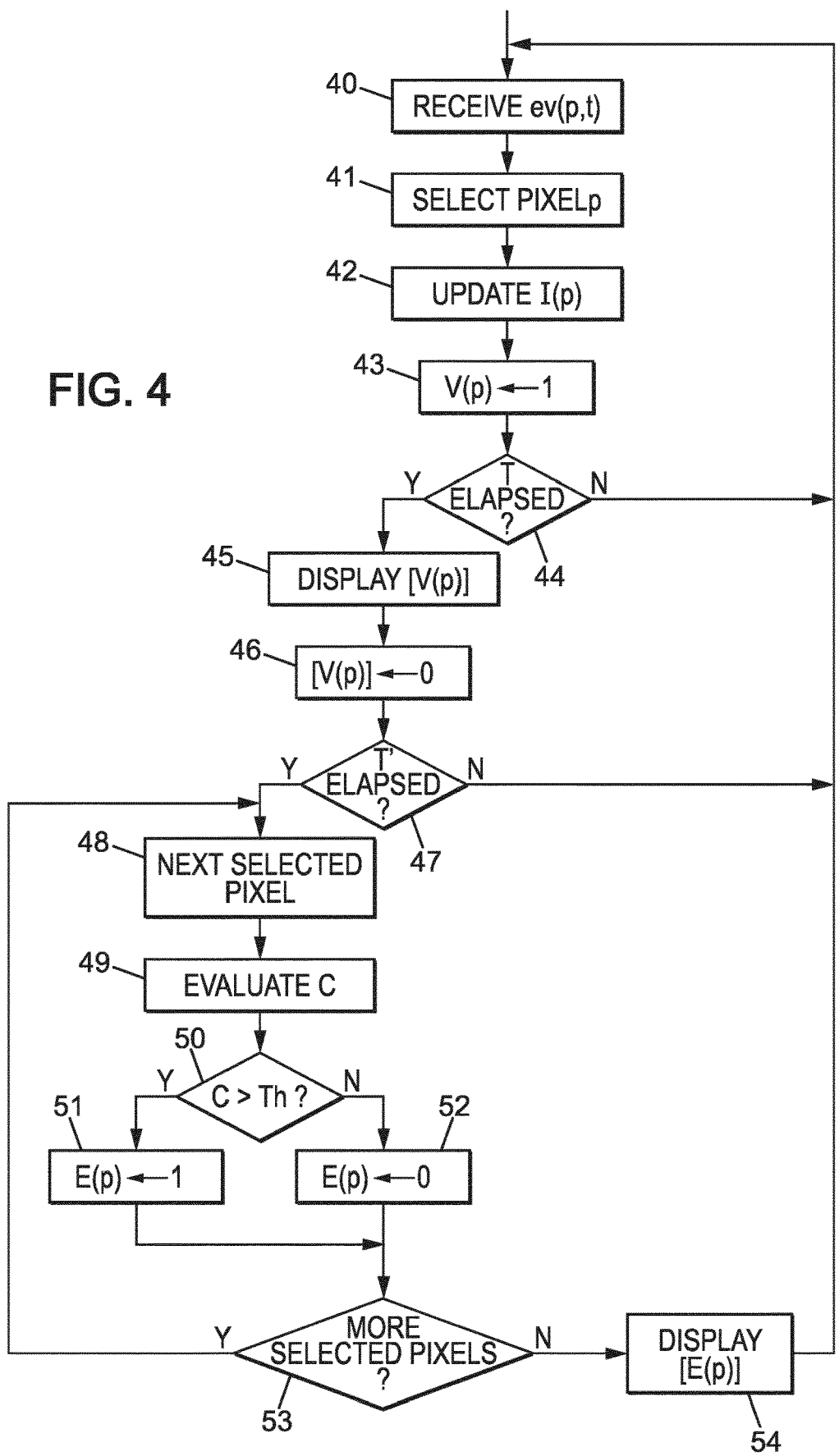
FIG. 4 is flow chart illustrating steps of an embodiment of the method for processing asynchronous signals.

The processing of the signal sequences produced from the sensing elements 16 of the light sensor 10 can be as illustrated in FIG. 4 in the case where both the event and contour representations are displayed.

Upon reception of an event ev(p, t) (step 40 of FIG. 4), e.g. a spike $P_0$ as shown in FIG. 2, the corresponding pixel p of the grayscale image is selected at step 41. The value I(p) of the selected pixel in the grayscale image is updated using the light level value contained in the event (step 42), encoded as the time difference δt between two spikes $P_1$ and $P_2$. The time-varying bit V(p) corresponding to that pixel in the matrix of the event representation is set to 1 at step 43 so as to display a dot at the position of the pixel in the event representation.

If the light modulator 30 is driven asynchronously, the pixel p for which V(p)=1 at step 43 can be displayed immediately. If the light modulator 30 is clocked to receive a frame of input bits periodically, the matrix [V(p)] in which some bits have been set to 1 during a period T is provided by the processor 20 at the end of that period T (test 44), so that the event representation is displayed (step 45). Then the matrix [V(p)] is reset to zero at step 46 for accumulating other events in the next period T.

The time resolution for displaying the contour representation will generally be coarser than the time resolution for displaying the event representation. Such condition is fulfilled if the event representation is provided asynchronously to the light modulator 30 while the contour representation is provided with some periodicity T'.

If the event representation is provided with a period T'>T, the event representation is provided with a period T'>T. For example, the period T' can be in a range of 1 to 100 milliseconds, more particularly in a range of 10 to 100 milliseconds while the period T is in a range of 1 microsecond to 10 milliseconds, more particularly in a range of 0.1 to 10 milliseconds. The exact values for the periods T and T' may be selected depending on the hardware used as the light modulator 30.

If, after resetting the matrix [V(p)] at step 46, the current period T' has not elapsed (test 47), the processor 20 returns to waiting for the next event ev(p, t). When the current period T' has elapsed, a contour processing is applied, illustrated as a loop 48-53 in FIG. 4.

That loop 48-53 is performed over the pixels p which have been selected at steps 41 during the elapsed period T'. The first, or a next, selected pixel p is considered at step 48 for evaluation of local contrast at step 49.

Various types of local contract measure C can be used in step 53. Typically, a respective group of adjacent pixels is defined for each selected pixel of the image for evaluation of the local contrast measure C. For instance, the pixels being arranged in a square array, the group of adjacent pixel of a given pixel p of position (x, y) can consist of the eight closest neighbors in the array. A vicinity of the pixel p is then defined as the pixel itself and those of its group of adjacent pixels. The vicinity is made of pixels at positions (x+α, y+β) where $α∈\{-1, 0, +1\}$ and $β∉\{-1, 0, +1\}$. An example of local contrast measure C is the absolute value of the difference between the maximum value $I_{max}$ and the minimum pixel value $I_{min}$ in the vicinity of the pixel: $C=|I_{max}-I_{min}|$. The above value C may be normalized with respect to the average pixel value in the vicinity.

Various other kinds of formulas can be used for evaluating the local contrast, for example by computing an approximation of the local gradient of the image intensity. As known in the art of image signal processing, Sobel kernels can be used, for example, for calculating such gradient approximations.

In step 50, the local contrast measure calculated in step 49 is compared to a threshold Th to decide whether the selected pixel p belongs to an edge or not. The value of the threshold Th may be adjusted depending on how contrasted the displayed edges should be.

If the threshold Th is exceeded in step 50, the selected pixel p is marked as being an edge pixel in step 51 (bit E(p) of the contour representation is set to '1'). Otherwise, it is marked as being a non-edge pixel in step 52 (bit E(p) is set to '0').

As long as there are remaining selected pixels for which the local contrast has not yet been evaluated (test 53), the next iteration in the loop is performed by returning to step 48. When all the selected pixels have been considered and evaluated, the update of the set of edge pixels following the period T' is finished, and the contour representation [E(p)] can be provided by the processor 20 to the light modulator 30 for display (step 54).

After the step 54 of displaying the contour representation, the matrix [E(p)] is not reset, so that the processor 20 keeps in memory the pixels which are determined to belong to edges in the scene. These pixels will be displayed again later as part of the contour representation if no changes of luminance occur to generate events in their neighborhood (no updates in steps 51-52). If new events occur at such a pixel location, the pixel will be selected again in a step 41 and its local contrast evaluated in a step 49 to determine whether it still belongs to an edge or not.

The embodiment shown in FIG. 4 corresponds to a case where the selected pixels evaluated in the contour processing loop 48-53 consist only of those which were selected in steps 41 in response to events included in event-based signal sequences received from the sensor 10.

In such a case, an alternative implementation includes evaluating the local contrasts C, comparing them to the threshold Th and deciding whether or not the pixel p is an edge pixel (E(p)=0 or 1) as part of the event processing, for example following step 42.

Alternatively, additional pixels may be selected for performing the contour processing 48-53 at every period T'. If we note [S(p)] a binary matrix of the selected pixels p, step 41 may consist in setting the bit S(p) to 1. The pixels checked in loop 48-53 are then those for which S(p)=1.

In an embodiment, after displaying the contour representation at step 54, the binary matrix [S(p)] is initialized for the next period T' with the value of the edge pixels which have just been displayed, that is [S(p)]=[E(p)]. In this case, the selected pixels which are evaluated in the contour processing loop 48-53 consist of those which were selected in steps 41 and also of the pixels of the previously determined set of edge pixels displayed at step 54.

According to another variant, the binary matrix [S(p)] is reset to zero after step 54 for the next period T'. At the end of the next period T', the binary matrix [S(p)] has 1's only at the pixels positions where events were received (step 40) during that period T'. Before performing the loop 48-53 after step 47, additional pixels are selected, namely those which are adjacent to the pixels selected in steps 41. For example, for each pixel p of position (x, y) for which S(p)=1, one also takes S(p')=1 before the loop 48-53 for all pixels p' of positions (x+α, y+β) where α∈{−1, 0, +1} and β∈{−1, 0, +1}. This makes it possible to check whether a change of luminance occurring at a pixel p changes the edge/non-edge status of the adjacent pixels p'.

The method as described above is typically implemented by programming the processor in any suitable computer language. The processor 20 is loaded with code instructions that control execution of steps such as those illustrated in FIG. 4.

It will be appreciated that the embodiments described above are illustrative of embodiments disclosed herein and that various modifications can be made without departing from the scope as defined in the appended claims.

In particular, the method of extracting contours from the output of an asynchronous event-based light sensor has applications other than in the field of vision restoration which was discussed above for illustration purposes. For example, the method disclosed has applications in the field of acquisition or real-time representation in environments with low energy and low data/memory bandwidth requirements. By using this method, an event-based sensor not only can capture motions and rapid changes in the environment but also can capture salient features and slow changes in the environment with a very low energy consumption and very low data and memory bandwidth. Potentially, the sensor and method can be used in forest protection, surveillance and monitoring—the rapid change being the detection of fire and movement of animals and humans; the slow change being the detection and counting of animals and humans, vegetation, in environment surveillance and monitoring, the rapid change being the detection of intrusion; the slow change being the vegetation growing, the detection of building deterioration and the person counting in a crowd—, or in vehicle camera—the rapid change being the environment monitoring while the vehicle is moving; the slow change being the detection of dangers and the environment monitoring while the vehicle is parked.

The invention claimed is:

1. A method for processing asynchronous signals generated by a light sensor, the light sensor having a matrix of sensing elements, the method comprising:
   receiving, from each sensing element of the matrix, a respective event-based signal sequence including events asynchronously produced as a function of variations of light incident on the sensing element and light level values respectively associated with at least some of the events;
   generating an image comprising pixels corresponding spatially to the sensing elements of the matrix; and
   repeatedly determining a set of edge pixels among the pixels of the image,
   wherein generating the image comprises updating each pixel of the image based on a light level value associated with a most recent event in the event-based signal sequence received from the sensing element corresponding to said pixel of the image,
   wherein determining the set of edge pixels comprises:
   selecting pixels of the image, wherein the selected pixels comprise pixels of the image corresponding to sensing elements from which the received event-based signal sequences include at least one event after a previous determination of the set of edge pixels, and pixels of the previously determined set of edge pixels;
   evaluating respective local contrast measures with respect to the selected pixels of the image; and
   deciding whether or not the selected pixels belong to the set of edge pixels based on the evaluated local contrast measures.

2. The method of claim 1, wherein the selected pixels comprise each pixel of the image corresponding to a sensing element from which the received event-based signal sequence includes at least one event after the previous determination of the set of edge pixels.

3. The method of claim 2, wherein the selected pixels further include each pixel of the previously determined set of edge pixels.

4. The method of claim 2, wherein the selected pixels consist only of the pixels selected in response to events included in the respective event-based signal sequences received from the sensing elements.

5. The method of claim 1, wherein the set of edge pixels is determined periodically, with a period in a range of 1 to 100 milliseconds, preferably in a range of 10 to 100 milliseconds.

6. The method of claim 1, further comprising outputting a contour representation as a matrix of time-varying bits, wherein each of the time-varying bits of the contour representation corresponds spatially to a respective pixel of the image and has a first value when the respective pixel of the image belongs to the set of edge pixels, and a second value when the respective pixel of the image does not belong to the set of edge pixels.

7. The method of claim 6, wherein the contour representation is used to control a light modulator.

8. The method of claim 6, wherein the contour representation is transmitted to a retinal implant for stimulation of retina cells.

9. A signal processing unit comprising:
an interface for connecting to a light sensor having a matrix of sensing elements and receiving, from each sensing element of the matrix, a respective event-based signal sequence including events asynchronously produced as a function of variations of light incident on the sensing element and light level values respectively associated with at least some of the events; and
a processor for generating an image comprising pixels corresponding spatially to the sensing elements of the matrix, and repeatedly determining a set of edge pixels among the pixels of the image,
wherein the processor is configured to update a respective pixel value of each pixel of the image based on a light level value associated with a most recent event in the event-based signal sequence received from the sensing element corresponding to said pixel of the image,
wherein the processor is configured to determine the set of edge pixels by:
selecting pixels of the image, wherein the selected pixels comprise pixels of the image corresponding to sensing elements from which the received event-based signal sequences include at least one event after a previous determination of the set of edge pixels, and pixels of the previously determined set of edge pixels;
evaluating respective local contrast measures with respect to the selected pixels of the image; and
deciding whether or not the selected pixels belong to the set of edge pixels based on the evaluated local contrast measures.

10. A computer program product comprising stored instructions to be executed in a processor associated with a light sensor having a matrix of sensing elements, wherein execution of the instructions by the processor controls steps of:
receiving, from each sensing element of the matrix, a respective event-based signal sequence including events asynchronously produced as a function of variations of light incident on the sensing element and light level values respectively associated with at least some of the events;
generating an image comprising pixels corresponding spatially to the sensing elements of the matrix; and
repeatedly determining a set of edge pixels among the pixels of the image,
wherein generating the image comprises updating each pixel of the image based on a light level value associated with a most recent event in the event-based signal sequence received from the sensing element corresponding to said pixel of the image,
wherein determining the set of edge pixels comprises:
selecting pixels of the image, wherein the selected pixels comprise pixels of the image corresponding to sensing elements from which the received event-based signal sequences include at least one event after a previous determination of the set of edge pixels, and pixels of the previously determined set of edge pixels;
evaluating respective local contrast measures with respect to the selected pixels of the image; and
deciding whether or not the selected pixels belong to the set of edge pixels based on the evaluated local contrast measures.

* * * * *